US006635087B2

(12) United States Patent
Angelucci et al.

(10) Patent No.: US 6,635,087 B2
(45) Date of Patent: Oct. 21, 2003

(54) LAMINOPLASTY IMPLANTS AND METHODS OF USE

(76) Inventors: Christopher M. Angelucci, 809 Summit Ave., Schwenksville, PA (US) 19473; Michael L. Boyer, II, 1708 E. Lancaster Ave., Paoli, PA (US) 19301; David C. Paul, 405 Greene La., Phoenixville, PA (US) 19460; Christopher J. Ryan, 2500 Hillcrest Rd., Drexel Hill, PA (US) 19026; Amit Sinha, 644 Drexel Ave., Drexel Hill, PA (US) 19026; Martin Walter, 300 Anglesey Ter., West Chester, PA (US) 19380

( * ) Notice: Subject to any disclaimer, the term of this patent is extended or adjusted under 35 U.S.C. 154(b) by 77 days.

(21) Appl. No.: 09/942,335

(22) Filed: Aug. 29, 2001

(65) Prior Publication Data

US 2003/0045936 A1 Mar. 6, 2003

(51) Int. Cl.[7] .................................................. A61F 2/44
(52) U.S. Cl. ............................... 623/17.11; 623/17.16; 606/61; 606/69
(58) Field of Search ............................ 623/17.11, 17.12, 623/17.13, 17.14, 17.15, 17.16; 606/60, 61, 69

(56) References Cited

U.S. PATENT DOCUMENTS

| 4,627,853 A | 12/1986 | Campbell et al. |
| 4,678,470 A | 7/1987 | Nashef et al. |
| 4,743,256 A | 5/1988 | Brantigan |
| 4,781,721 A | 11/1988 | Grundei |
| 4,820,305 A | 4/1989 | Harms et al. |
| 4,834,757 A | 5/1989 | Brantigan |
| 4,877,020 A | 10/1989 | Vich |
| 4,892,545 A | * 1/1990 | Day et al. .................. 623/17.11 |
| 4,950,296 A | 8/1990 | McIntyre |
| 5,015,255 A | 5/1991 | Kuslich |
| 5,053,049 A | 10/1991 | Campbell |
| 5,112,354 A | 5/1992 | Sires |
| 5,133,718 A | 7/1992 | Mao |
| 5,147,361 A | 9/1992 | Ojima et al. |
| 5,147,404 A | 9/1992 | Downey |

(List continued on next page.)

FOREIGN PATENT DOCUMENTS

| DE | 19630256 | 1/1998 |
| EP | 4093698 | 7/1992 |
| EP | 0599766 | 6/1994 |
| EP | 1103236 | 5/2001 |

(List continued on next page.)

OTHER PUBLICATIONS

Michael F. O'Brien et al., "A Novel Technique for Laminoplasty Augmentation of Spinal Canal Area Using Titanium Miniplate Stabilization, A Computerized Morphometric Analysis," *Spine*, vol. 21(4), pp. 474–483, Feb. 1996.
Wilkins, "Clinical Effectiveness of Demineralized Bone Matrix Assayed in Human Cell Culture," *Advances in Tissue Banking*, pp. 113–124, 1999.
Application Ser. No. PCT/US02/27139.

*Primary Examiner*—Pedro Philogene
(74) *Attorney, Agent, or Firm*—Pennie & Edmonds, LLP

(57) ABSTRACT

Implants for use in the spinal column are disclosed. The implants comprise a bone allograft coupled with a non-allogenic plate. The plate has ends that fasten to opposing spine segments, and an intermediate portion that engages the allograft using deformable fingers, or with a hollow portion sized to receive and hold part of the allograft, or with fixed tabs. Methods of using the implants are also disclosed.

32 Claims, 13 Drawing Sheets

U.S. PATENT DOCUMENTS

| | | |
|---|---|---|
| 5,192,327 A | 3/1993 | Brantigan |
| 5,211,661 A | 5/1993 | Shinjou et al. |
| 5,236,460 A | 8/1993 | Barber |
| 5,290,312 A | 3/1994 | Kojimoto et al. |
| 5,306,309 A | 4/1994 | Wagner et al. |
| 5,360,430 A | 11/1994 | Lin |
| 5,413,602 A | 5/1995 | Metz-Stavenhagen |
| 5,425,772 A | 6/1995 | Brantigan |
| 5,439,684 A | 8/1995 | Prewett et al. |
| 5,458,638 A | 10/1995 | Kuslich et al. |
| 5,458,641 A | 10/1995 | Ramirez Jimenez |
| 5,514,180 A | 5/1996 | Heggeness et al. |
| 5,534,031 A | 7/1996 | Matsuzaki et al. |
| 5,571,109 A | 11/1996 | Bertagnoli |
| 5,571,190 A | 11/1996 | Ulrich et al. |
| 5,609,635 A | 3/1997 | Michelson |
| 5,658,337 A | 8/1997 | Kohrs et al. |
| 5,683,463 A | 11/1997 | Godefroy et al. |
| 5,683,464 A | 11/1997 | Wagner et al. |
| 5,702,449 A | 12/1997 | McKay |
| 5,716,415 A | 2/1998 | Steffee |
| 5,728,159 A | 3/1998 | Stroever et al. |
| 5,766,251 A | 6/1998 | Koshino |
| 5,766,252 A | 6/1998 | Henry et al. |
| 5,776,199 A | 7/1998 | Michelson |
| 5,814,084 A | 9/1998 | Grivas et al. |
| 5,824,088 A | 10/1998 | Kirsch |
| 5,860,973 A | 1/1999 | Michelson |
| 5,861,041 A | 1/1999 | Tienboon |
| 5,865,845 A | 2/1999 | Thalgott |
| 5,865,846 A | 2/1999 | Bryan et al. |
| 5,879,385 A | 3/1999 | Crockard et al. |
| 5,888,222 A | 3/1999 | Coates et al. |
| 5,888,227 A | 3/1999 | Cottle |
| 5,888,228 A | 3/1999 | Knothe et al. |
| 5,895,426 A | 4/1999 | Scarborough et al. |
| 5,972,368 A | 10/1999 | McKay |
| 5,980,572 A * | 11/1999 | Kim et al. ............... 623/17.16 |
| 5,984,967 A | 11/1999 | Zdeblick et al. |
| 5,989,289 A | 11/1999 | Coates et al. |
| 6,008,433 A | 12/1999 | Stone |
| 6,015,436 A | 1/2000 | Schonhoffer |
| 6,019,793 A | 2/2000 | Perren et al. |
| 6,025,538 A | 2/2000 | Yaccarino, III |
| 6,033,438 A | 3/2000 | Bianchi et al. |
| 6,039,762 A | 3/2000 | McKay |
| 6,045,580 A | 4/2000 | Scarborough et al. |
| 6,059,829 A | 5/2000 | Schlapfer et al. |
| 6,066,175 A * | 5/2000 | Henderson et al. ...... 623/17.11 |
| 6,074,423 A | 6/2000 | Lawson |
| 6,080,157 A * | 6/2000 | Cathro et al. ................. 606/61 |
| 6,086,613 A | 7/2000 | Camino et al. |
| 6,090,998 A | 7/2000 | Grooms et al. |
| 6,096,080 A | 8/2000 | Nicholson et al. |
| 6,096,081 A | 8/2000 | Grivas et al. |
| 6,099,531 A | 8/2000 | Bonutti |
| 6,106,557 A | 8/2000 | Robioneck et al. |
| 6,111,164 A | 8/2000 | Rainey et al. |
| 6,113,603 A | 9/2000 | Medoff |
| 6,143,030 A | 11/2000 | Schroder |
| 6,143,031 A | 11/2000 | Knothe et al. |
| 6,143,033 A | 11/2000 | Paul et al. |
| 6,149,651 A | 11/2000 | Drewry et al. |
| 6,156,037 A | 12/2000 | LeHuec et al. |
| 6,159,211 A | 12/2000 | Boriani et al. |
| 6,176,882 B1 | 1/2001 | Biedermann et al. |
| 6,200,347 B1 | 3/2001 | Anderson et al. |
| 6,206,923 B1 | 3/2001 | Boyd et al. |
| 6,206,924 B1 | 3/2001 | Timm |
| 6,214,050 B1 | 4/2001 | Huene |
| 6,231,610 B1 * | 5/2001 | Geisler .................... 623/17.11 |
| 6,235,059 B1 * | 5/2001 | Benezech et al. ........ 623/17.16 |
| 6,241,770 B1 | 6/2001 | Michelson |
| 6,241,771 B1 | 6/2001 | Gresser et al. |
| 6,245,108 B1 | 6/2001 | Biscup |
| 6,248,109 B1 | 6/2001 | Stoffella |
| 6,258,125 B1 * | 7/2001 | Paul et al. ............... 623/17.11 |
| 6,261,586 B1 | 7/2001 | McKay |
| 6,270,528 B1 | 8/2001 | McKay |
| 6,277,149 B1 | 8/2001 | Boyle et al. |
| 6,283,968 B1 | 9/2001 | Mehdizadeh |
| 6,287,343 B1 | 9/2001 | Kuslich et al. |
| 6,294,187 B1 | 9/2001 | Boyce et al. |
| 6,296,665 B1 | 10/2001 | Strnad et al. |
| RE37,479 E | 12/2001 | Kuslich |
| 6,358,254 B1 | 3/2002 | Anderson |
| 6,371,986 B1 | 4/2002 | Bagby |
| 6,432,106 B1 * | 8/2002 | Fraser ......................... 606/61 |
| 2001/0000803 A1 | 5/2001 | Gielen et al. |
| 2001/0001129 A1 | 5/2001 | McKay et al. |
| 2001/0005796 A1 | 6/2001 | Zdeblick et al. |
| 2001/0008980 A1 | 7/2001 | Gresser et al. |
| 2001/0010021 A1 | 7/2001 | Boyd et al. |
| 2001/0011191 A1 | 8/2001 | Kohrs |
| 2001/0014831 A1 | 8/2001 | Scarborough |
| 2001/0016774 A1 | 8/2001 | Bresina et al. |
| 2001/0016775 A1 | 8/2001 | Scarborough et al. |
| 2001/0016777 A1 | 8/2001 | Biscup |
| 2002/0120335 A1 | 8/2002 | Angelucci et al. |

FOREIGN PATENT DOCUMENTS

| | | | |
|---|---|---|---|
| FR | 2727003 | 5/1996 | |
| FR | 2727004 | 5/1996 | |
| FR | 2727005 | 5/1996 | |
| FR | 2736538 | 1/1997 | |
| FR | 2782914 | 3/2000 | |
| JP | 5208029 | 8/1993 | |
| JP | 408010276 A | 1/1996 | |
| JP | 409075381 A | 3/1997 | |
| JP | 10179622 | 7/1998 | |
| JP | 410179622 A * | 7/1998 | ............... 623/17.11 |
| JP | 410286272 A | 10/1998 | |
| JP | 411004840 A | 1/1999 | |
| JP | 2000139970 A | 5/2000 | |
| JP | 2000152951 A | 6/2000 | |
| JP | 2000152952 A | 6/2000 | |
| JP | 2000175943 A | 6/2000 | |
| JP | 2000175944 A | 6/2000 | |
| WO | WO 92/01428 | 2/1992 | |
| WO | WO 97/09940 | 3/1997 | |
| WO | WO 98/17209 | 4/1998 | |
| WO | WO 99/09914 | 3/1999 | |
| WO | WO 99/38461 | 8/1999 | |
| WO | WO 00/07527 | 2/2000 | |
| WO | WO 00/07528 | 2/2000 | |
| WO | WO 00/13615 | 3/2000 | |
| WO | WO 00/41654 | 7/2000 | |
| WO | WO 00/41655 | 7/2000 | |
| WO | WO 00/42954 | 7/2000 | |
| WO | WO 00/45747 | 8/2000 | |
| WO | WO 00/74607 | 12/2000 | |
| WO | WO 01/08611 | 2/2001 | |
| WO | WO 01/15637 | 3/2001 | |
| WO | WO 01/47443 | 7/2001 | |
| WO | WO 01/49219 | 7/2001 | |

* cited by examiner

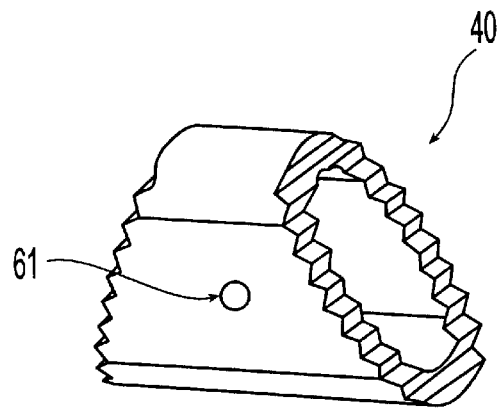
Fig. 5A
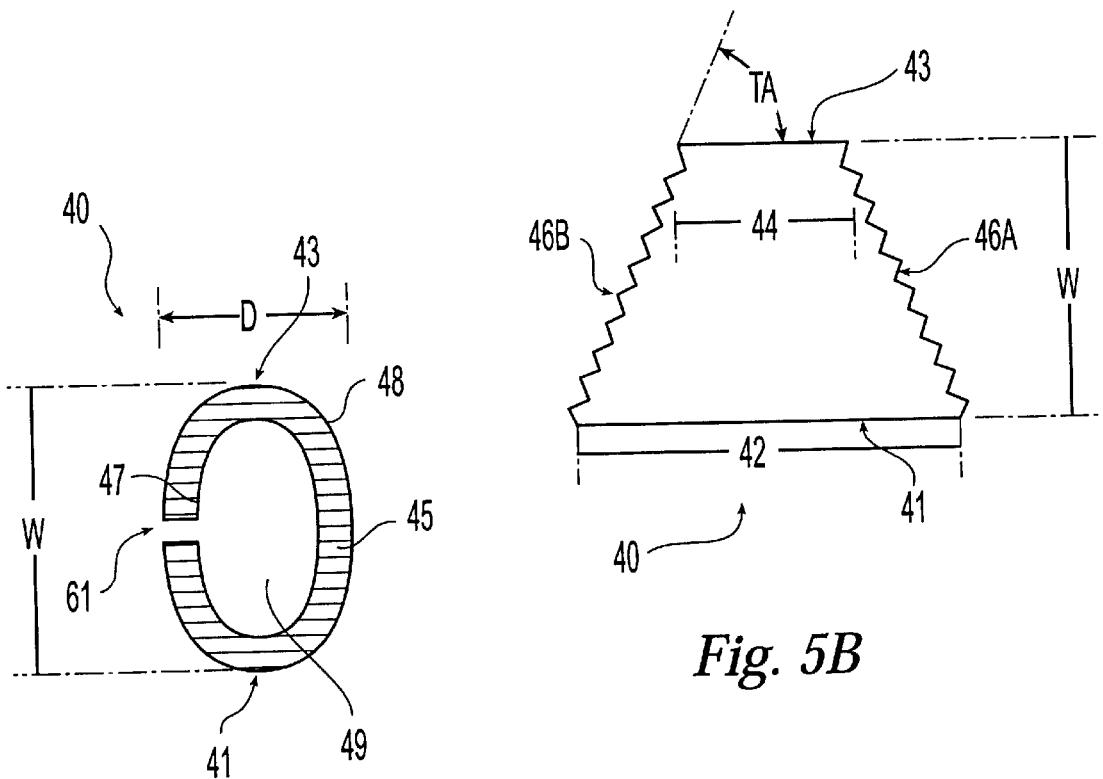
Fig. 5B
Fig. 5C

LAMINOPLASTY IMPLANTS AND METHODS OF USE

TECHNICAL FIELD

The present invention relates to a medical implant and method, and, more particularly, to an improved surgical implant and method for expanding the spinal canal to eliminate pressure on the spinal cord caused by an impinging vertebral bone.

BACKGROUND OF THE INVENTION

Various medical conditions may result in a reduction of the area within the vertebrae available for the spinal cord. Spinal stenosis is one such condition involving the narrowing of the canal in the center of the spine through which the spinal cord and nerve roots run. Spinal stenosis may result when the ligaments of the spine thicken and calcify (harden from deposits of calcium salts), or when bones and joints enlarge, and osteophytes (bone spurs) form. A herniated (bulging) disk may also place pressure on the spinal cord or nerve root. Furthermore, diseased bone or tumors may result in an ingrowth into the spinal cord area. This decreases the space (neural foramen) available for nerve roots leaving the spinal cord.

Two surgical methods currently exist to create additional room in the spinal canal. The first is called a laminectomy, and involves removal of the lamina (roof) of one or more vertebrae. A limitation of the laminectomy procedure is that it involves removal of the supporting structures at the back of the vertebrae which align the spinal column. The result may be that a patient suffers some postural deformity. To prevent such postural problems, a graft may be installed between the ends of the removed bone to span the void and reinstate the necessary support. The second procedure is called a laminoplasty, in which the targeted vertebra is cut, spread apart and a graft is inserted to permanently enlarge the space. Unlike the laminectomy, typically no bone material is excised during the laminoplasty procedure. Two different laminoplasty procedures are currently used. The first is called the unilateral or "open door" laminoplasty in which one side (lamina) of the vertebra is cut all the way through, while the other side is cut only half way to create a hinge. The vertebral element is then rotated about the hinge, and the graft is inserted into the opening, increasing the opening of the spinal canal. The second procedure is called the bilateral or "French door" laminoplasty in which the midline of the vertebra (spinous process) is cut all the way through, and the lamina are cut half way through, creating two hinges. The vertebral element is then opened at the bisected spinous process, and a graft inserted into the opening, again increasing the opening of the spinal canal.

Various materials may be used for the grafts installed during laminoplasty procedures. U.S. Pat. No. 6,080,157 to Cathro et al. and U.S. Pat. No. 5,980,572 to Kim et al. disclose the use of titanium, ceramic and nylon inserts. Further, using allografts taken from long bones such as the femur, humerus, tibia and fibula, for spinal fusion procedures is known, as disclosed by U.S. Pat. No. 5,728,159 to Stroever et al. Allografts, as such bone grafts are called, are removed from a donor and processed using known techniques to preserve the allograft until implantation. Allografts have mechanical properties which are similar to the mechanical properties of vertebrae even after processing. The benefit of such property matching is that it prevents stress shielding that occurs with metallic implants. Allografts, unlike magnetic metals, are also compatible with magnetic resonance imaging (MRI) procedures, allowing more accurate ascertainment of fusion. Furthermore, allografts are naturally osteogenic providing excellent long term fusion with the patient's own bone.

Several different spacer designs have been used in laminoplasty procedures to the present. For example, the Cathro patent discloses a metal, nylon or teflon spacer for use in a unilateral laminoplasty procedure. The Cathro spacer is a rectangular plate having shouldered edges which engage the ends of the cut lamina, and is held in place by a spring mechanism. The difficulty with the Cathro spacer is that its operation relies on the continued satisfactory operation of the installed spring. Further, the Cathro device provides little available area for the packing of fusion enhancing (i.e. osteogenic) material. The Kim patent discloses a spacer for use in a bilateral laminoplasty procedure. The Kim spacer consists of inner and outer trapezoidal segments joined together by a rectangular segment. The tapered surface of the inner trapezoidal segment is designed to conform to the inner surface of the split spinous process halves, while the taper of the outer segment is designed to assume the shape of the removed spinous process tip. The Kim spacer seats on the resulting flat surface of bone. Like the Cathro device, the Kim device provides little area in which to pack osteogenic material to facilitate bone-implant fusion. Neither the Cathro nor Kim device use allograft as a spacer material, which may result in reduced propensity for fusion and the possibility for stress shielding.

Accordingly, there is a need in the art to provide implants and methods for both laminectomy and unilateral and bilateral laminoplasty procedures, which provide excellent dimensional, strength and retention capability, which enhance fusion with the patient's own bone, which are easy to select, fit and install and which provide excellent compatability with post-operative imaging (MRI).

SUMMARY OF THE INVENTION

The implants of present invention are provided for use in the spinal column. In one embodiment, the implants comprise an allograft fabricated from cancellous bone material and a member formed of non-allograft material having first and second bone engaging portions and an allograft engaging portion. The graft engaging portion may be configured to retain the allograft when the allograft contacts the graft engaging portion.

The graft engaging portion may comprise at least one raised tab. Further, the implant member may have a central region between the first and second bone engaging portions and the at least one raised tab angled inward toward the central region of the member. The allograft may have first and second ends, each comprising bone engaging portions, where at least one of the bone engaging portions is comprised of partially, substantially, or fully demineralized bone. At least one of the implant member bone engaging portions may comprise a suture attachment portion configured to allow a surgeon to secure the member bone connecting portions to the first and second bone segments.

In a different embodiment, an implant is provided for use in maintaining a desired distance between a first spinal bone cut end and a second spinal bone cut end, in which the implant comprises an allograft having a body and first and second ends, and a plate formed of a non-allograft material having an intermediate portion and first and second ends, where the intermediate portion has an allograft engaging portion configured to retain the allograft, and where the first and second ends of the plate have bone engaging portions which themselves have fastener receiving portions. The allograft engaging portion is configured to engage the allograft body and the bone engaging portions are configured to engage respective outer surfaces of first and second spinal bone cut ends. The allograft first and second ends are configured to contact the first and second cut bone ends. In a specific embodiment, the allograft engaging portion may comprise deformable fingers configured to engage the graft. In another specific embodiment, the allograft engaging portion may comprise a hollow portion, where the allograft has a shape complementary to the hollow portion, and where the hollow portion is configured to at least partially receive the allograft. In a further embodiment, the allograft first and second ends comprise bone engaging portions, at least one of which may comprise partially, substantially, or fully demineralized bone.

A method for providing a desired distance between first and second cut bone ends of the spine is also provided. This method comprising the steps of: cutting a vertebra to produce first and second cut bone ends; separating the bone ends to define a space therebetween; providing an allograft having a body and first and second ends; providing a plate formed of a non-allograft material having an intermediate portion and first and second ends, where the intermediate portion has an allograft engaging portion configured to retain the allograft, the first and second plate ends have bone engaging portions with fastener receiving portion, and where the allograft engaging portion is configured to engage the allograft body, the bone engaging portions are adapted to engage the first and second bone outer surfaces, and the allograft first and second ends are configured to contact the first and second cut bone ends, then engaging the allograft engaging portions of the plate with the allograft; engaging the bone engaging portions with respective cut bone ends; providing at least two bone fasteners; inserting at least one fastener into the fastener receiving portion of each bone engaging portion; and engaging the at least one bone fasteners with said cut bone end. In a further embodiment, the step of cutting a vertebra may comprise cutting all the way through one lamina. In a further embodiment, the adjacent lamina further may be cut half way through.

BRIEF DESCRIPTION OF THE DRAWINGS

The features and advantages of the implant and method of use will become more readily apparent from the following detailed description of the invention in which like elements are labeled similarly and in which:

FIGS. 5A, 5B and 5C are perspective, side and end views of a third embodiment of the implant, for use in a bilateral laminoplasty procedure;

DETAILED DESCRIPTION OF THE PREFERRED EMBODIMENTS

Preferred embodiments, features and aspects of an implant adapted to be used in unilateral and bilateral laminoplasty procedures are described, in which a portion of a targeted vertebra is cut, the space available for the spinal cord and associated nerves is expanded, and an implant is installed between the cut segments of bone.

Figure 1A:
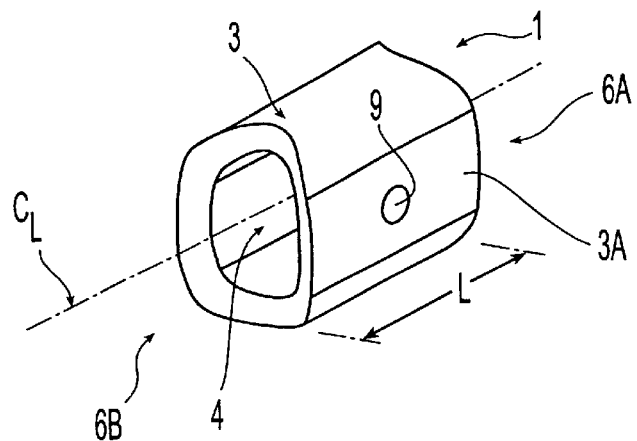
FIGS. 1A, 1B and 1C are perspective, end and top views of the first embodiment of the implant, for use in a unilateral laminoplasty procedure.
Figure 1B:
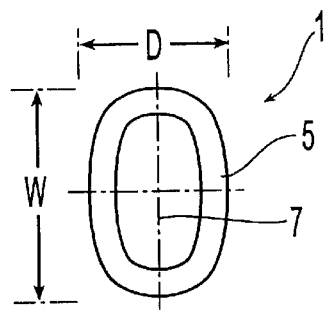
Figure 1C:
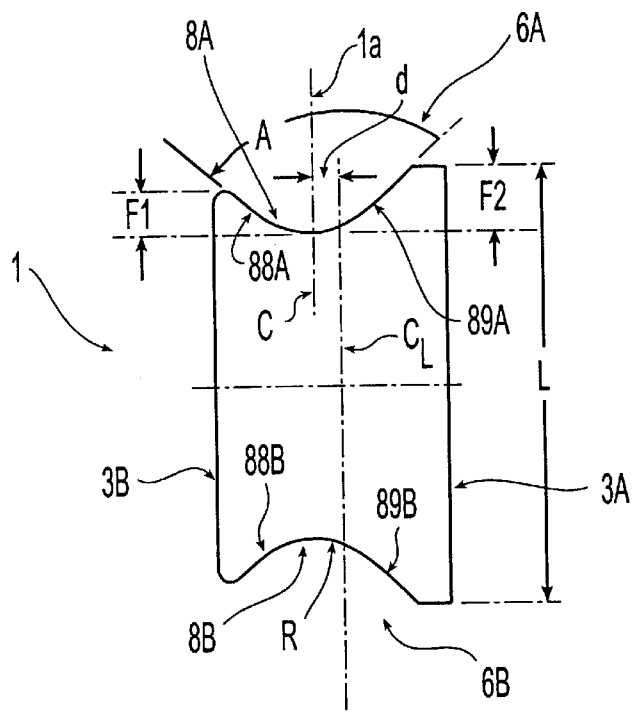

Referring more particularly to the drawings, FIGS. 1A, 1B and 1C show an implant for use in a unilateral or "open door" laminoplasty. The implant 1 has a longitudinal axis "CL," a length "L," a wall 5 defining an outside surface 3 and an inside surface 4, and first and second ends 6A, 6B. Inside surface 4 communicates with first and second ends 6A, 6B to define a hollow central region 7 of the implant. Outside surface 3 has an outer side region 3A and an inner side region 3B such that when the implant is installed between cut segments of lamina, outer side region 3A faces outward away from the spinal canal, while inner side region 3B faces inward toward the spinal canal. The implant 1 further has a depth "D" which is the distance between outer side region 3A and inner side region 3B. Implant 1 also has a width "W" which is the distance between opposing outer surfaces 3 measured along a drawn line perpendicular to a line defining the depth "D." Length "L" preferably should be between about 11.5 millimeters (mm) to about 15.5 mm; depth "D" preferably should be between about 5.5 mm to about 6.5 mm; and width "W" preferably should be between about 8.0 mm to about 9.5 mm.

The shape and size of outside surface 3 is not critical and, therefore, any implant configuration can be used preferably so long as the first and second ends 6A, 6B provide sufficient contact area with the lamina ends, and the implant 1 does not interfere with other anatomy, and does not intrude on the spinal cord space. In a preferred embodiment, however, the outside surface 3 is configured such that the shape of the implant, when viewed from the end, displays the form of a substantially geometric shape (e.g. ellipse, oval, circle, etc.). In this embodiment the exterior dimensions of the implant also approximate those of the outside surface of the cut lamina segments between which the implant is installed. Although implants having cross sections of greater or lesser proportion than the lamina to which they attach will function properly, for aesthetic purposes and in an attempt to minimize the amount of material introduced into a patient's body, the outer surface of the implant should preferably not extend beyond the outer surface of the adjoining bone.

In a further embodiment, the inside surface 4 of the implant 1 may be machined so that the hollow central region 7 approximates the configuration and geometry of the implant exterior (i.e. form an ellipse or oval shape). The hollow central region may be designed to be packed with osteogenic material such as bone chips, etc. to facilitate fusion of the implant with the patient's lamina. Preferably, the central region may be as large as possible to enhance fusion of the implant to the patient's lamina. The thickness of wall 45 preferably should be between about 1.00 to about 1.50 mm; more preferably about 1.25 mm. Preferably the thickness of wall 5 should not be less than about 1.0 mm to ensure the implant retains sufficient strength to withstand the stresses imparted on the spine.

The implant 1 may be fabricated from a biocompatable metal (e.g. stainless steel, or titanium, etc.) or polymer, or from allograft material preferably taken from a long bone (e.g. femur, tibia, fibula, humerus). Where the implant is an allograft, the inside surface 4 and hollow central region 7 may be defined by the intermedullary canal of the donor bone. The hollow center may be left as such, or the inner surface 4 may be machined, as with other implant materials, to maximize the space available for packing with osteogenic material. Again, the thickness of the implant wall 5, preferably is not reduced to less than about 1.00 mm.

During the unilateral laminoplasty procedure, the targeted lamina is cut in half and the segment attached to the spinous process is rotated or swung out to increase the area available for the spinal cord and associated nerves. Subsequent to this rotation, the lamina segments no longer reside along the same axis, but instead the ends are disposed at an angle with respect to each other. Implant 1 is substantially straight along its length, and so to accommodate this angular displacement of the lamina, first and second ends 6A, 6B incorporate arcuate cutouts 8A, 8B to grasp and retain the cut lamina segments. Viewed from the top of the implant (FIG. 1C), these arcuate cutouts 8A, 8B are generally concave and may be circular in shape, or they may consist of a cutout spanning an obtuse angle and converging to a small radius at the crotch of the first and second ends 6A, 6B. Arcuate cutouts 8A, 8B have a centerline 1a which runs parallel to the longitudinal axis of the implant 1. The centerline 1a of the arcuate cutouts may be coexistent with the longitudinal axis of the implant 1, or it may be offset with respect to that axis to further improve retention of the cut and displaced lamina ends. In a further embodiment, the centerlines 1a of the arcuate cutouts may each be offset on an opposite side of the implant centerline to facilitate retention of the implant in cases where the angle between the cut and spread lamina is more severe, such as when the surgeon spreads the lamina segments as wide as possible to provide maximum additional space for the spinal cord and associated nerves.

In the preferred embodiment, shown in FIG. 1C, each arcuate cutout 8A, 8B comprises first angled faces 88A, 89A and second angled faces 88B, 89B, respectively, which meet at crotch "C" to form a face angle "A." Preferably, face angle A is about 100 degrees. Crotch radius "R," comprises the transition between the first and second angled faces. Crotch radius "R" is preferably about 2 mm. Each arcuate cutout further comprises first and second face depths "F1" and "F2." The first and second face depths are a measure of the depth of the crotch relative to the inner side region 3B and outer side region 3A of the implant, and will be different lengths whenever the centerline 1a of the arcuate cutout is offset from the centerline "CL" of the implant 1. Preferably first face depth "F1" is about 1.25 mm, and second face depth "F2" is about 1.5 mm. Each arcuate cutout 8A, 8B also has a centerline offset "d," which is the degree to which the arcuate cutout 8A, 8B is shifted from the centerline "CL" of the implant 1. Preferably, the centerline offset "d" is from about 0 to 2.5 mm toward the inner side region 3B of implant 1. The face depth "F1" of the first and 6A of the implant 1 may be the same or different than the face depth "F1" of the second end 6B. Likewise, the face depth "F2" of the first end 6A may be the same or different than the face depth "F1" of the second end 6A.

In a further embodiment of the implant comprising allograft material, first and second ends 8A, 8B may comprise regions of partially, substantially, or fully demineralized cortical bone to further facilitate fusion of the implant to the lamina. Preferably the demineralized bone portion comprises the entire surface of each first and second end 6A, 6B of the implant 1. Preferably, the depth of the demineralized portion will be up to about 2 mm.

The implants further may incorporate at least one suture hole 9 in the implant wall 5 to allow the surgeon the option of suturing the implant to the cut lamina ends. These suture holes 9 may vary in number and size, with the only limitation being that they should not be so large or numerous as to compromise the strength or integrity of the implant.

Figure 2A:
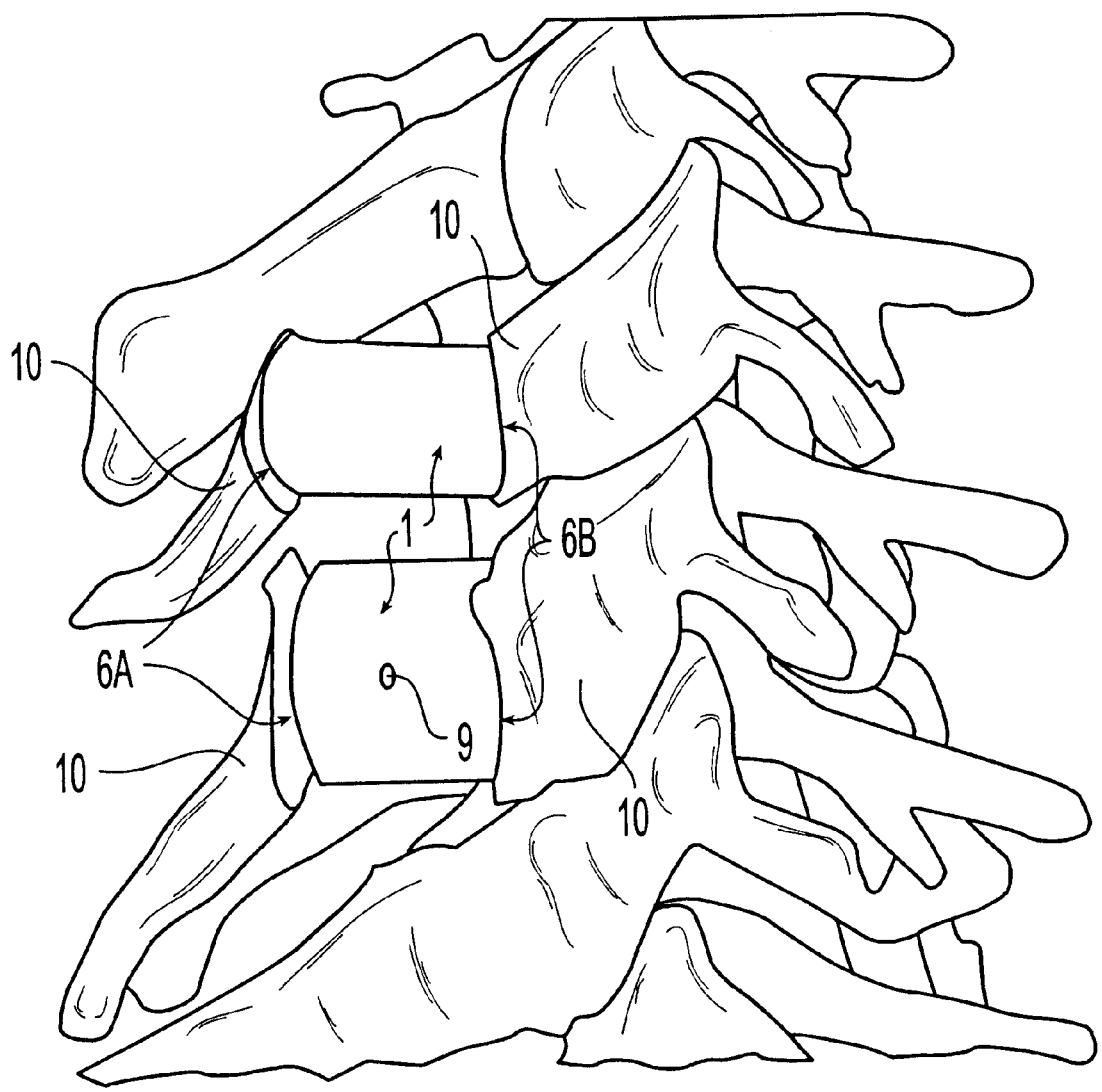
FIGS. 2A and 2B are side and top views of the implant of FIG. 1 installed between the cut lamina segments of a vertebra during a unilateral laminoplasty procedure.
Figure 2B:
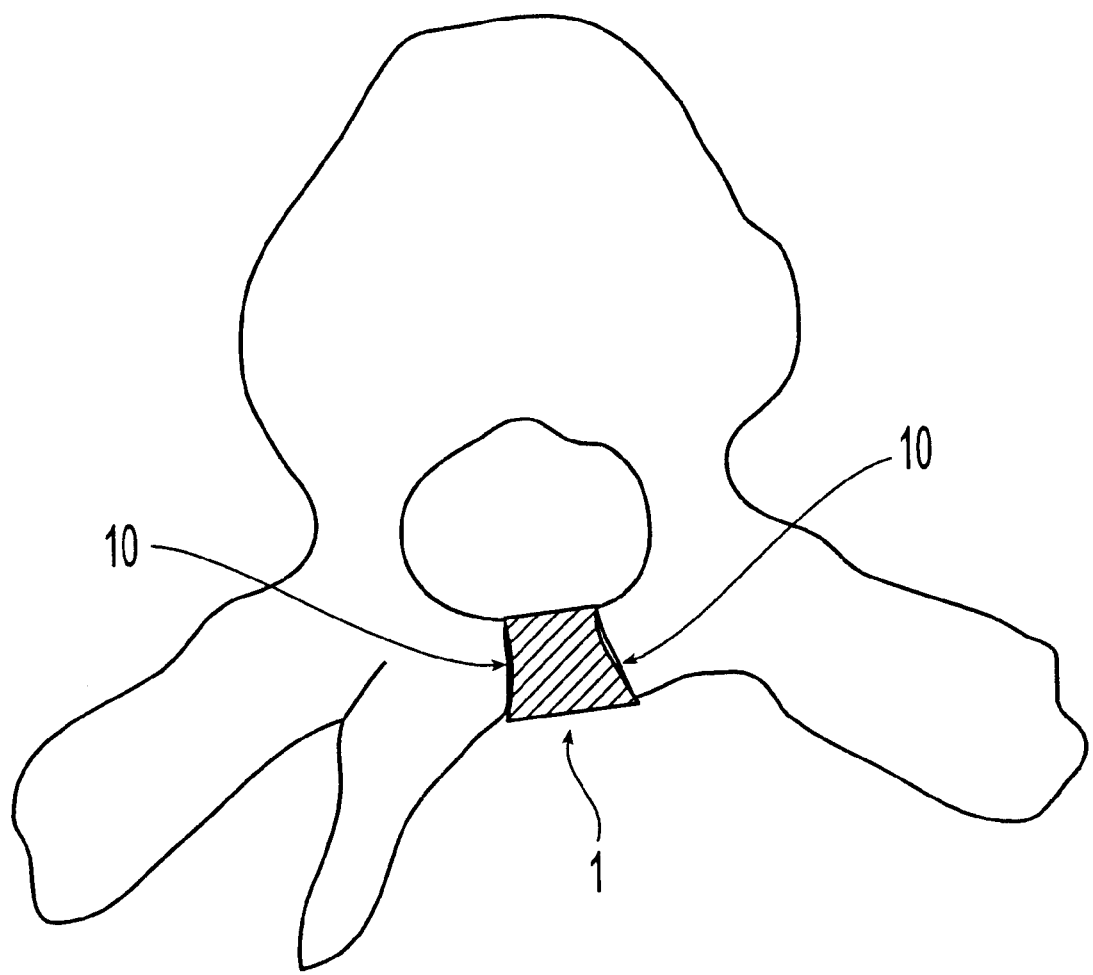

FIGS. 2A and 2B are side and top views of the implant of FIG. 1 installed in a patient between the cut lamina ends in a unilateral laminoplasty procedure. In FIG. 2A two different sized implants 1 are installed on the cut lamina segments 10 of adjacent vertebrae, to illustrate application of the implant design to bones of different size. FIG. 2B shows the interaction between the implant and the cut vertebra segments 10.

Figure 3A:
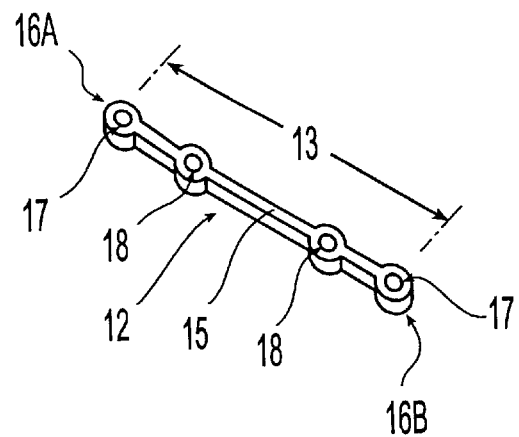
FIGS. 3A and 3B are a perspective view of a retaining plate of the present invention, and a side view of two such retaining plates installed over the implants of FIGS. 2A and 2B.

The design of the bone engaging ends 6A, 6B of the implants 1 are sufficient to ensure retention of the implants 1 between the cut ends of lamina 10. Some surgeons, however, desire an additional measure of assurance that the implants 1 will not loosen or otherwise be expelled from between the lamina ends 10. The implant, therefore, provides for the optional installation of a plate 12 to be secured over an installed implant in a unilateral laminoplasty procedure. FIG. 3A is a perspective view of a plate 12 which may be installed to secure the implant 1 of FIGS. 1 & 2, to ensure the implant 1 is not expelled from the cut lamina ends 10. Plate 12 has a length 13, a thickness 14 and a body portion 15 with first and second ends 16A, 16B comprising bone engaging portions 17 and implant engaging portions 18. As shown in FIG. 3A the bone engaging portions 17 and implant engaging portions 18 may consist of the holes adapted for receiving bone screws 19 or hooks 20 (not shown) capable of grasping bone screws installed in the lamina and/or implant. Each side of plate 12 may have one or more bone engaging portions 19 and one or more implant engaging portions 18. In a further embodiment the plate 12 may be flexible to allow the surgeon to form it to the individual contour of the patient's spine, thereby achieving a tight fit between components. The plates may be fabricated from a biocompatible metal or other material known in the art that would be suitable for long term retention of an implant 1.

Instead of a single plate 12, smaller plates without connecting body portion 15 may be utilized, each plate comprising at least one bone engaging portion 17 and one implant engaging portion 18.

Figure 3B:
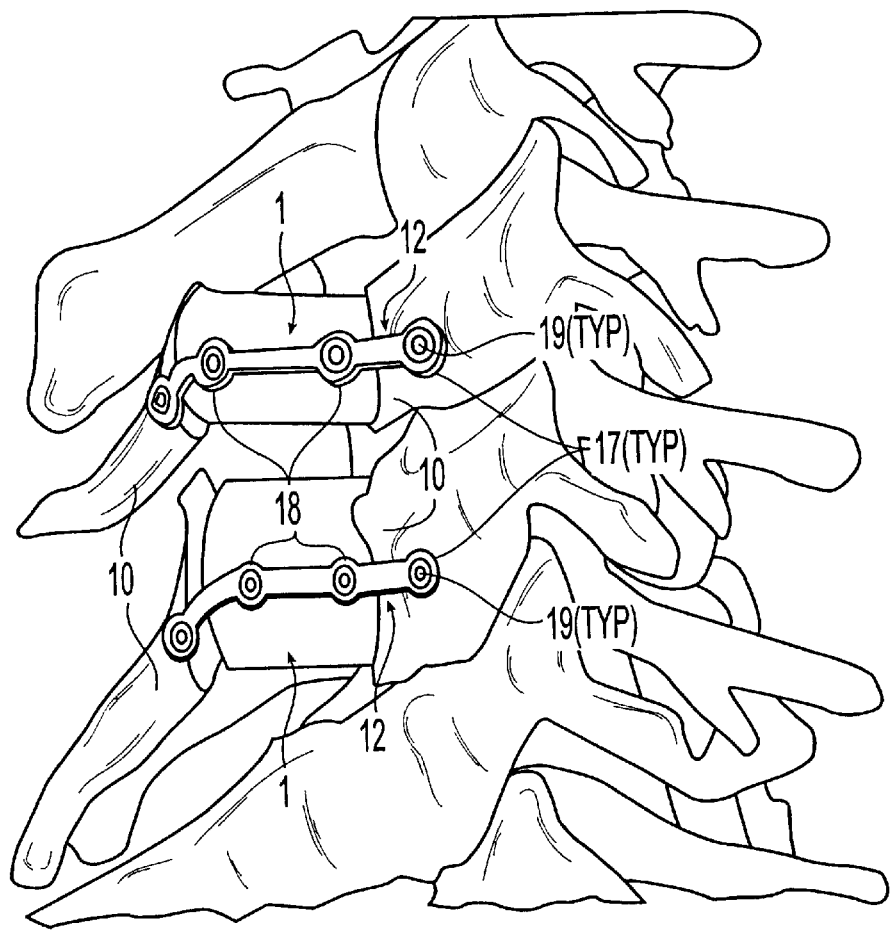

FIG. 3B is a side view of the implants 1 installed in FIG. 2A, further showing the installation of optional plates 12 of FIG. 3A. Bone screws 19 are installed to secure the plates 12 to both the respective opposing lamina segment 10, and the implant. In this embodiment, bone screws are also installed in the screw holes 18 of the implant engaging portion, to secure the plates to the implants 1. Also in this embodiment, the plates are flexible and are bent to assume the varying contour of the lamina segments and the implant. More than one optional plate may be used to secure the implant to the lamina.

Figure 4A:
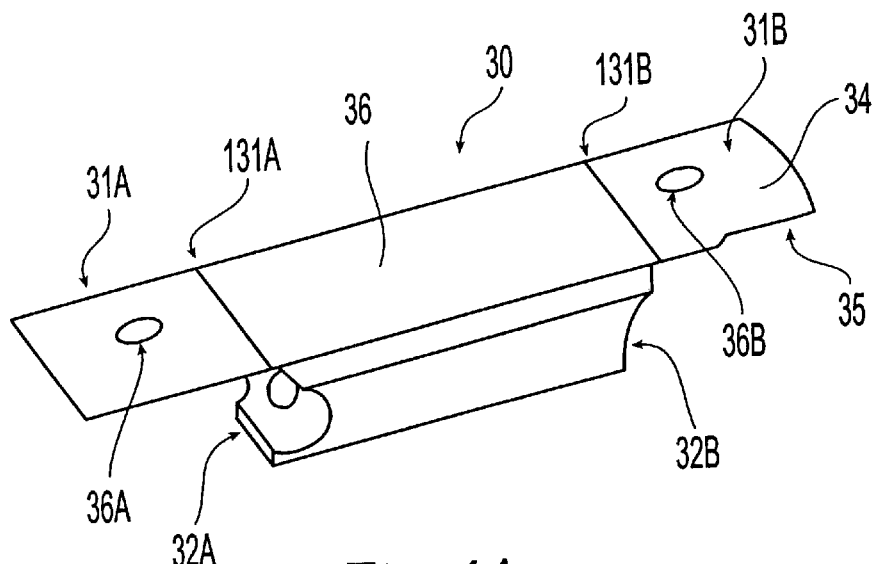
FIGS. 4A and 4B are perspective and side views of a second embodiment of the implant, a unilateral implant incorporating demineralized bone flaps.
Figure 4B:
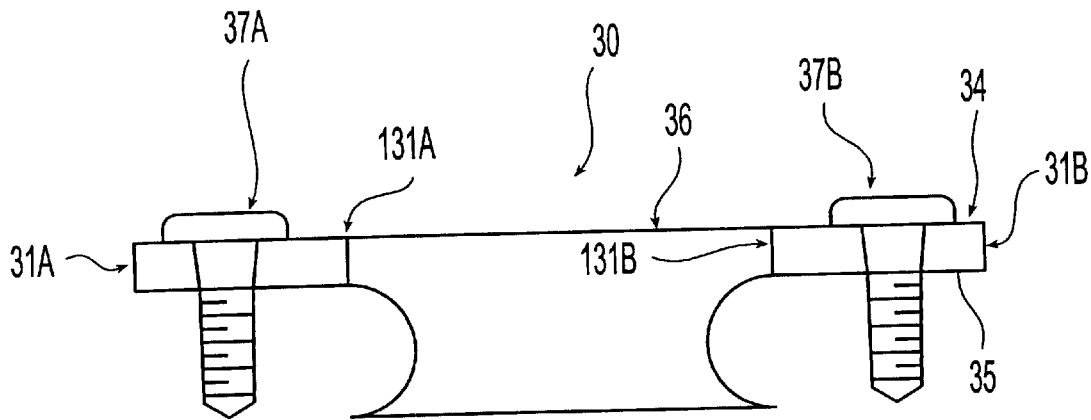

FIGS. 4A and 4B show perspective and side views of an allograft implant 30 which incorporates the design features of the implants of FIG. 1, but which further includes a pair of bone flaps 31A, 31B disposed at first and second ends 32A, 32B of the implant 30. These bone flaps are used to secure the implant 30 to the respective cut ends of lamina in a unilateral laminoplasty procedure. At least a portion of each flap comprises demineralized bone. Demineralization of the flaps, but not the implant, provides the implant with flexible attachment points which may be contoured to conform to the shape of the adjacent lamina. Bone flaps 31A, 31B comprise thin, flat, rectangular segments of allograft having an outer surface 34 and a bone engaging surface 35. The outer surfaces 34 of the flaps preferably are the same width as, are contiguous with, and extend axially like wings from the outer surface 36 of the implant 30. In a preferred embodiment, bone flaps 31A, 31B are machined from the same segment of donor bone as implant 30. At least a portion of flaps 31A, 31B may be demineralized using any commercially acceptable process (e.g. hydrochloric acid bath, etc.) that will render the resulting flaps flexible. Flaps 31A, B are provided with holes 36A, 36B suitable for receiving bone screws 37A, 37B which are used to secure the bone flaps 31A, 31B and implant 30 to the adjacent cut lamina ends.

In another embodiment, these bone flaps may not be demineralized, but instead each bone flap may comprise a notch 131A, 131B in the respective region where the bone flaps 31A, 31B connect to the implant 30. Notches 131A, 131B may be any type of notch or reduction in the thickness of the bone flap appropriate to provide flexibility for placing the flaps on the adjacent laminae surfaces, while retaining the requisite strength to ensure the bone flaps will not separate from the implant during installation.

FIGS. 5A, 5B and 5C show an embodiment of an implant for use in a bilateral or "french door" laminoplasty procedure, in which the spinous process of a targeted vertebra is bisected along the sagittal plane and the segments separated to enlarge the spinal canal. The implant 40 has a wall 45 having an inside surface 47 and an outside surface 48, and first and second ends 46A, 46B. The outside surface 48 has an outer side region 41 having an outer side length 42 and an inner side region 43 having an inner side length 44. Inside surface 47 communicates with first and second ends 46A & 46B to define a hollow central region 49 of the implant. The implant 40 has a generally trapezoidal shape when viewed from the side (FIG. 5B), and inner side region forms angle "TA" with respect to the first and second ends 46A, 46B. This trapezoidal configuration allows the implant first and second ends 46A, 46B to conform to the cut, angled surfaces of the spinous process segments to which the implant will eventually fuse. Inner side length 44 preferably is from between about 6.0 mm to about 10 mm, and angle "TA" preferably is from between about 50 to about 70 degrees.

The shape and size of outside surface 48 is not critical and, therefore, any implant external configuration can be used preferably so long as first and second ends 46A, 46B provide sufficient contact area with the cut spinous process segments, does not project out from between the bone segments so far as to interfere with other anatomy, and does not intrude on the spinal cord space For aesthetic purposes and in an attempt to minimize the amount of new material introduced into a patient, however, the outside surface 41 of the implant 40 should preferably not extend beyond the outside surface of the cut spinous process segments. In a preferred embodiment the outside surface 41 of the implant 40 is configured such that the outside surface 41, when viewed from the end, displays the form of a substantially geometric shape (e.g. ellipse, oval, circle, etc.) (FIG. 5C).

In a further embodiment, the inside surface 43 of the implant 40 may be machined so that the hollow central region 49 approximates the configuration and geometry of the implant outside surface 41 (i.e. an ellipse or oval). The hollow central area is designed to be packed with osteogenic material such as bone chips, etc. to facilitate fusion of the implant with the patient's cut spinous process segments. Preferably, this center area may be made as large as possible to facilitate the fusion process.

The thickness of wall 45 preferably should be from between about 1.00 to about 1.50 mm; more preferably about 1.25 mm. Preferably the thickness of wall 45 should not be less than about 1.0 mm to ensure the implant retains sufficient strength to withstand the stresses imparted on the spine associated with daily living.

The implant 40 may be fabricated from a biocompatable metal (e.g. stainless steel, or titanium, etc.) or polymer, or from allograft material preferably taken from a long bone (e.g. femur, tibia, fibula, humerus). Where the implant is fabricated from metal or polymer, it may be provided in a solid form. Preferably, however, the implant should incorporate a hollow region, and the inside surface 44, should be formed to maximize the space available for packing with osteogenic material while maintaining adequate wall thickness. Where the implant is an allograft, the inside surface 44 and hollow center 49 may be defined by the intermedullary canal of the donor bone. The allograft may be left in this state, and the hollow central region 49 packed with osteogenic material. Preferably, however, the inside surface 44 of the allograft will be machined and the hollow central region 49 enlarged to maximize the space available for packing with osteogenic material.

Figure 6A:
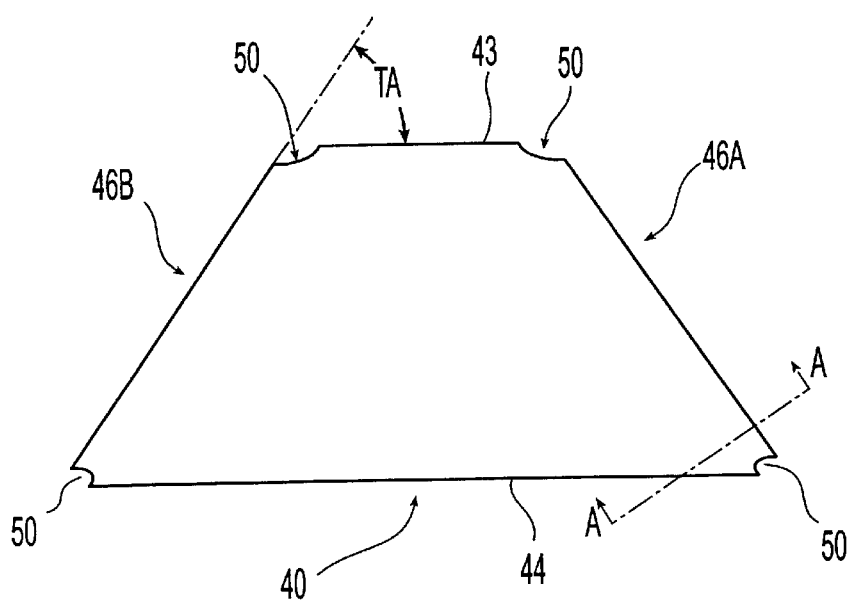
FIGS. 6A and 6B are side and section views of the implant of FIG. 5 showing the incorporation of a channel to accept the corresponding arms of a set of distractor pliers used to install the implant.
Figure 6B:
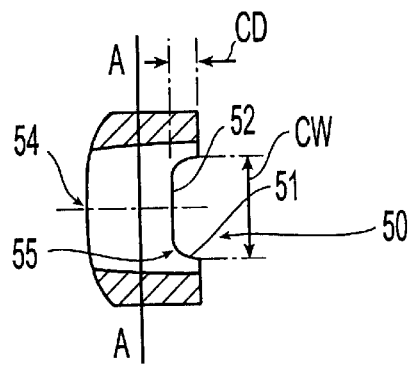

FIGS. 6A and 6B show first and second ends 46A, 46B of implant 40 each incorporating a channel 50 to accept the corresponding arms of a set of distractor pliers (not shown) which may be used to separate the bisected spinous process segments during the bilateral laminoplasty procedure. Each channel 50 has two sidewalls 51 each having a depth "CD", a bottom surface 52 having a width "CW" and a centerline 54 which is formed by a line extending along the implant 40 from inner side surface 43 to outer side surface 41. Preferably, each channel 50 may incorporate a radiused transition 55 between the sidewalls 51 and the bottom surface 52. In a further preferred embodiment, the channel runs from the inner side surface 43 to the outer side surface 41 of each end 46A, 46B of the implant. The specific dimensions of the channels is not critical, but should be configured to accept the distractor arms used during the distraction and insertion portion of the procedure. Preferably, the channel bottom surface width "CW" is about 4 mm, and the sidewall depth "CD" is about 1 mm.

Figure 7:
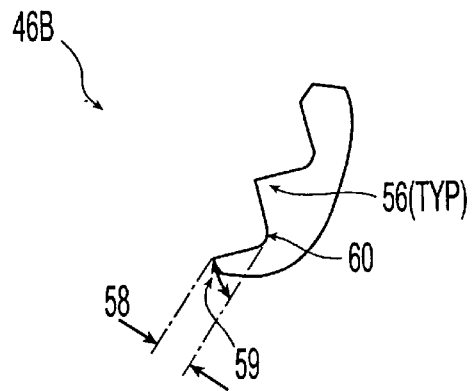
FIG. 7 is a detail view of the end of the implant of FIG. 5B showing a preferred embodiment of the surface projections used to facilitate retention of the implant between cut spinous process segments.

FIG. 7 shows a further embodiment of bilateral laminoplasty implant 40, in which first and second ends 46A, 46B comprise surface projections to improve pre-fusion retention of the implant 40 between respective cut spinous process segments. In a preferred embodiment, a plurality of saw-tooth serrations 56 having a height 58 and a tooth angle 59 are provided. Preferably the serrations are oriented to run vertically when the implant 40 is installed in the patient. Height 58 and tooth angle 59 are defined with respect to the respective planes formed by implant first and second ends 46A, 46B. Height 58 is measured from the trough 60 of each serration, while tooth angle is measured from the plane formed by the implant first and second ends 46A, 46B. Preferably, height 58 is about 0.5 mm, tooth angle 59 is about 45 degrees, and the distance between troughs 60 is about 1.2 mm. While these dimensions and profile are preferred, other suitable surface profiles (e.g. pyramidal teeth, etc.) may be used to ensure implant retention.

In a further embodiment of the implant 40 comprising allograft material, first and second ends 46A, 46B may comprise regions of partially, substantially, or fully demineralized cortical bone to further facilitate fusion of the implant to the lamina. Preferably the partially, substantially, or fully demineralized bone portion may comprise the entire surface of each first and second ends 46A, 46B of the implant 40. Preferably the depth of the demineralized portion of will be up to about 2 mm.

The implant 40 may also incorporate a plurality of sutures holes 61 (see FIG. 5C) formed through the implant wall 45 to allow the surgeon to secure the implant to the cut spinous process segments. These suture holes 61 may vary in number, size and position, with the only limitation being that their size, position and number preferably should not compromise the strength and integrity of the implant.

Figure 8A:
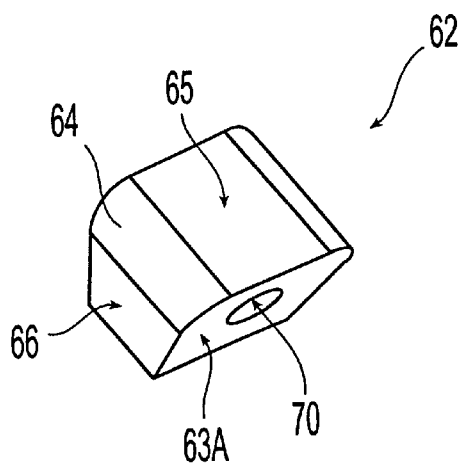
FIGS. 8A, 8B and 8C are perspective, end and side views of a fourth embodiment of the implant, for use in a bilateral laminoplasty procedure.
Figure 8B:
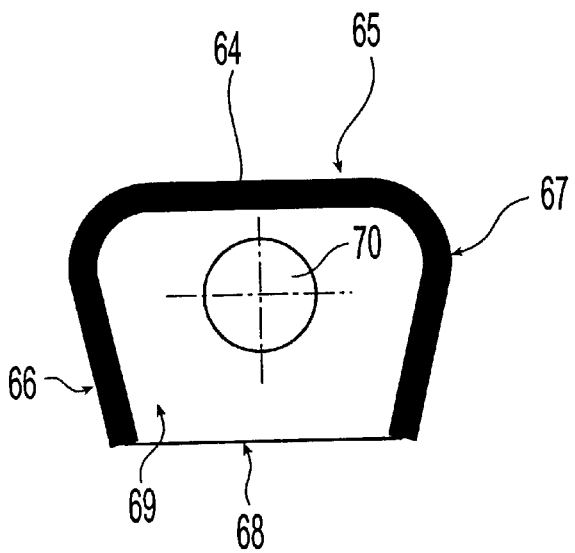
Figure 8C:
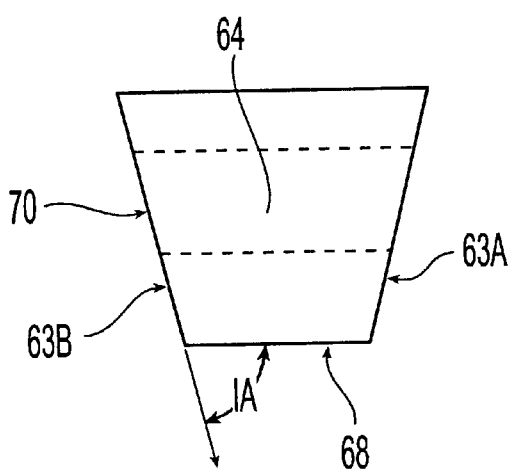

FIGS. 8A, 8B and 8C show a further embodiment of an implant for use in a bilateral laminoplasty procedure. Implant 62 has a first and second ends 63A, 63B, an inner side region 68, an outer side region 65, and sides 66 and 67. The implant 62, like the implant of FIG. 5, has a generally trapezoidal shape when viewed from the side (FIG. 8C). Again, this trapezoidal configuration allows the implant first and second ends 63A, 63B to conform to the cut, angled surfaces of the spinous process segments to which the implant will eventually fuse. As such, inner side 68 forms angle "IA" with respect to the first and second ends 63A, 63B. In this embodiment, the implant 62 is an allograft, comprising "tri-cortical" bone taken from the crest of the ilium region of the pelvis. Harvesting bone from this segment of the pelvis provides an implant which naturally comprises a thin region 64 of cortical bone on outer side 65, and sides 66 & 67. The inner side 68 of the implant, as well as the implant body portion 69 comprise cancellous bone. This combination of bone types allows the surgeon to exploit both the good strength characteristics of cortical bone, and the good osteogenic characteristics of cancellous bone in a single implant. In a further embodiment, the implant 62 comprises a cavity 70 which communicates with implant first and second ends 63A & 63B, and which may be used for packing osteogenic material to promote fusion between the implant and the cut spinous process segments.

In a preferred embodiment of the implant 62 of FIG. 8, the implant first and second ends 63A, 63B comprise surface projections to improve pre-fusion retention of the implant 62 between respective cut spinous process segments. Saw-tooth serrations, similar to those illustrated and described with regard to the implant of FIG. 5, may be provided. Again, other suitable surface profiles (e.g. pyramidal teeth, etc.) may also be provided to ensure implant retention.

In a further embodiment of the implant 62 comprising allograft material, first and second ends 63A, 63B may comprise regions of partially, substantially, or fully demineralized cortical bone to further facilitate fusion of the implant to the lamina. Preferably the demineralized bone portion may comprise the entire surface of each first and second ends 63A, 63B of the implant 62. Preferably, the depth of the demineralized portion of will be up to about 2 mm.

In another embodiment, the implant 62 may incorporate a plurality of sutures holes (not shown) similar to those shown in FIG. 5C, to allow the surgeon to secure the implant to the cut spinous process segments. These suture holes may vary in number, size and position, with the only limitation being that their number, size and position should not compromise the strength and integrity of the implant.

Figure 9A:
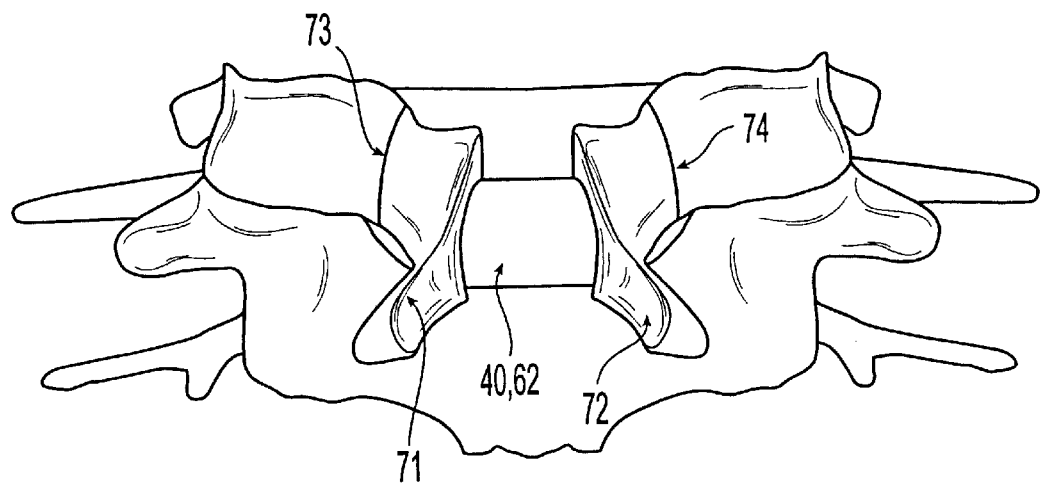
FIGS. 9A and 9B are front and top views of the implants of FIGS. 7 and 8 installed between the cut spinous process segments of a vertebra during a bilateral laminoplasty procedure.
Figure 9B:
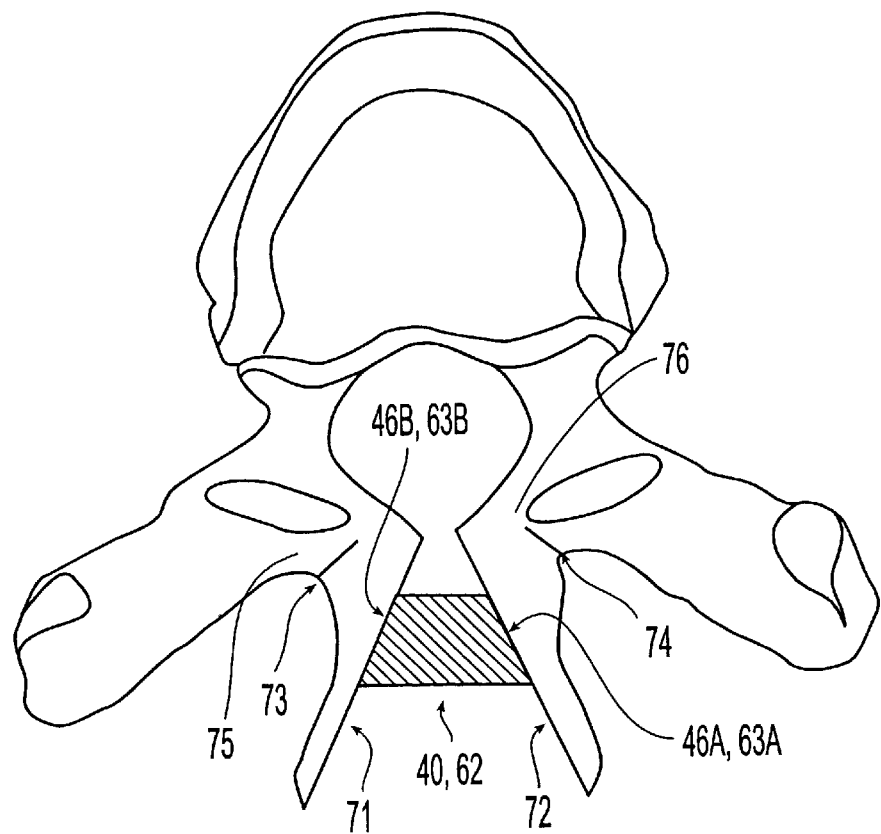

FIGS. 9A and 9B are front and top views of either trapezoidal implants 40, 62 of FIGS. 5, 8 installed in a patient. First and second ends 46A, 46B, 63A, 63B of implant 40, 62 contact cut spinous process segments 72 and 71 respectively. Hinge cuts 73 and 74 in lamina 75, 76 enable the spinous process segments to be "swung out" by the surgeon to facilitate insertion of the implant 40, 62 therebetween.

Figure 10A:
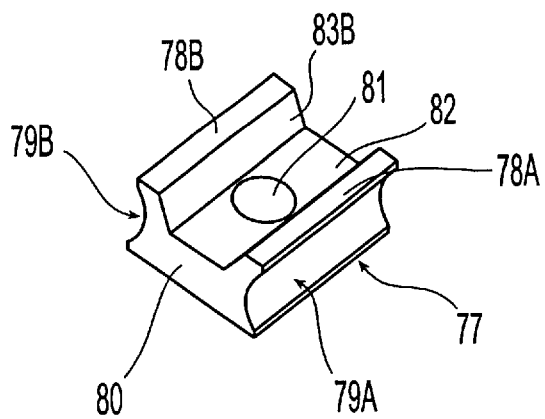
FIGS. 10A, 10B and 10C are perspective, end and top views of a fifth embodiment of the implant, for use in a unilateral laminoplasty procedure.
Figure 10B:
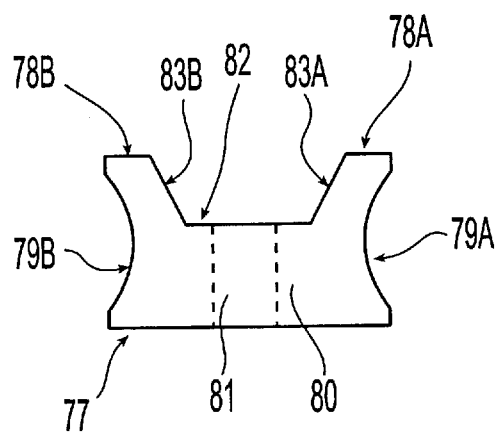
Figure 10C:
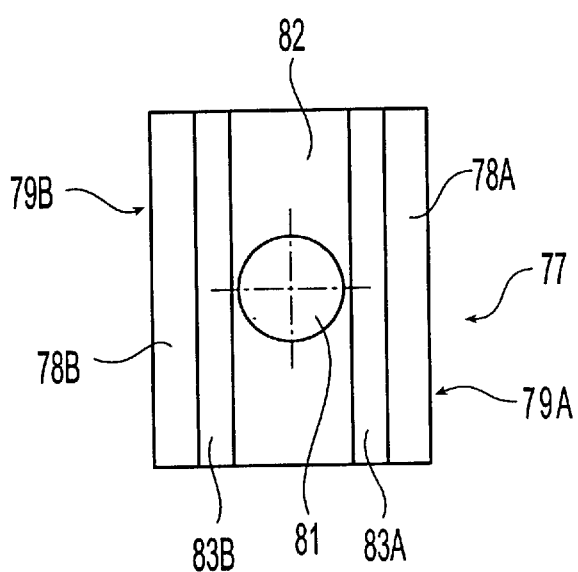

FIGS. 10A, 10B and 10C show a further embodiment of an implant adapted for use in a unilateral laminoplasty procedure. Implant 77 comprises first and second plate portions 78A, 78B for connecting to the opposing segments of cut lamina produced during a unilateral laminoplasty procedure. First and second plate portions 78A, 78B are connected by an intermediate portion 80. The plate portions further comprise respective first and second bone engaging portions 79A, 79B which are configured to engage the opposing cut lamina segments. In a preferred embodiment, first and second bone engaging portions 79A, 79B comprise arcuate surfaces for engaging and cradling the respective cut lamina ends. Arcuate surfaces are particularly suited for this purpose because their concave shape can engage and retain lamina segments residing along different axes, a phenomenon which occurs during the unilateral laminoplasty procedure when a single lamina is cut and the resulting segments are swung out to enlarge the area available for the spinal cord. The swinging out process results in an angle being formed between the segments, and it is this misalignment which the arcuate surfaces of the bone engaging portions 79A & 79B accommodate.

In a further embodiment, the thickness of the intermediate portion 80 may be smaller than the height of the first and second plate portions 78A, 78B.

Implant 77 may be fabricated from any biocompatible metal (e.g. titanium, stainless steel, etc.) or polymer, or the implant may be formed of allograft material. If allograft is used, the implant 77 preferably should be fabricated from cortical bone.

In a further embodiment of the implant 77 comprising allograft material, first and second bone engaging portions 79A, 79B may comprise regions of partially, substantially, or fully demineralized cortical bone to further facilitate fusion of the implant to the lamina segments. Preferably the demineralized bone portion may comprise the entire surface of each first and second bone engaging portions 79A, 79B. Preferably, the depth of the demineralized portion will be up to about 2 mm.

In another embodiment, the implant 77 may incorporate suture hole 80 to allow the surgeon to secure the implant to the cut spinous process segments. Additional suture holes (not shown) may be provided, and may vary in number, size and position, with the only limitation being that their size, position and number preferably should not compromise the strength and integrity of the implant 77.

Figure 11A:
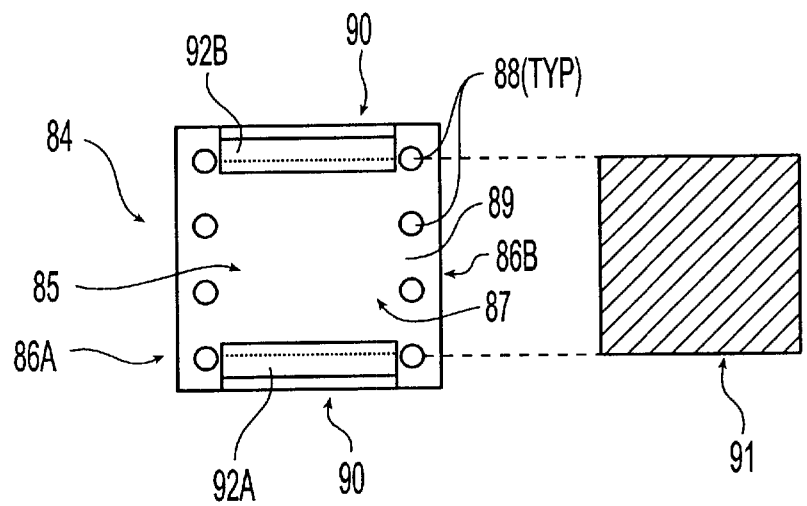
FIGS. 11A, 11B and 11C are top, side and end views of a sixth embodiment of the implant, for use in a unilateral laminoplasty procedure.
Figure 11B:
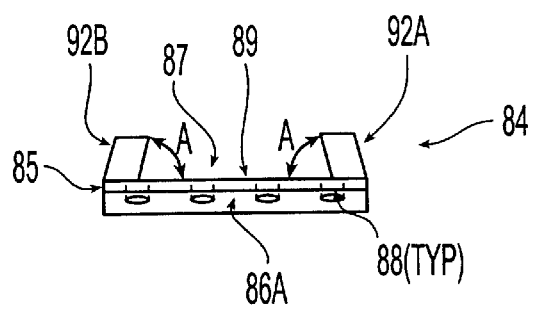
Figure 11C:
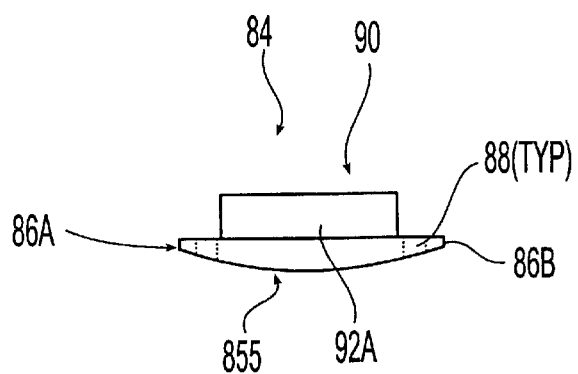

FIGS. 11A, 11B and 11C show a further embodiment of an implant adapted for use in a unilateral laminoplasty procedure. Implant 84 comprises a plate portion 85 having bone engaging portions 86A, 86B, a graft engaging portion 87, and an allograft 91. Bone engaging portions 86A, 86B further comprise a plurality of suture holes 88 configured to allow the surgeon to secure the cut lamina segments to bone engaging portions 86A, 86B Graft engaging portion 87 comprises a graft seating surface 89 and a graft retaining portion 90 configured to retain a correspondingly shaped allograft 91 for engaging the opposing cut lamina segment. In a preferred embodiment, graft retaining portion 90 comprises two raised tabs 92A, 92B, each residing along at least a portion of opposing ends of graft seating surface 89. In a preferred embodiment, raised tabs 92A, 92B are angled slightly toward the center of graft seating surface 89 so as to facilitate retention of allograft 91. Preferably the angle "A" between raised tabs 92A, 92B and graft seating surface 89 will be from about 70 to about 80 degrees; more preferably this angle will be about 75 degrees. Plate portion 85 further comprises a bottom surface 85S. When installed, graft 91 comprises the inner side surface of the implant (i.e. the surface which is closest to the spinal canal), while plate bottom surface 85S comprises the outer side surface of the implant (i.e. the surface which faces away from the spinal canal). In a preferred embodiment, bottom surface 85S comprises a convex shape which assumes the rounded contour of the lamina segments. Preferably, this convex surface has a radius of about 18 mm.

Plate portion 85 may be fabricated from any biocompatible metal (e.g. titanium, stainless steel, etc.) or polymer, or it may be made of allograft material. If allograft is used, the plate portion 85 may be fabricated from cortical bone. Graft 91 preferably may be comprised of a cancellous type bone material to facilitate fusion of the implant to the patient's lamina.

Figure 12A:
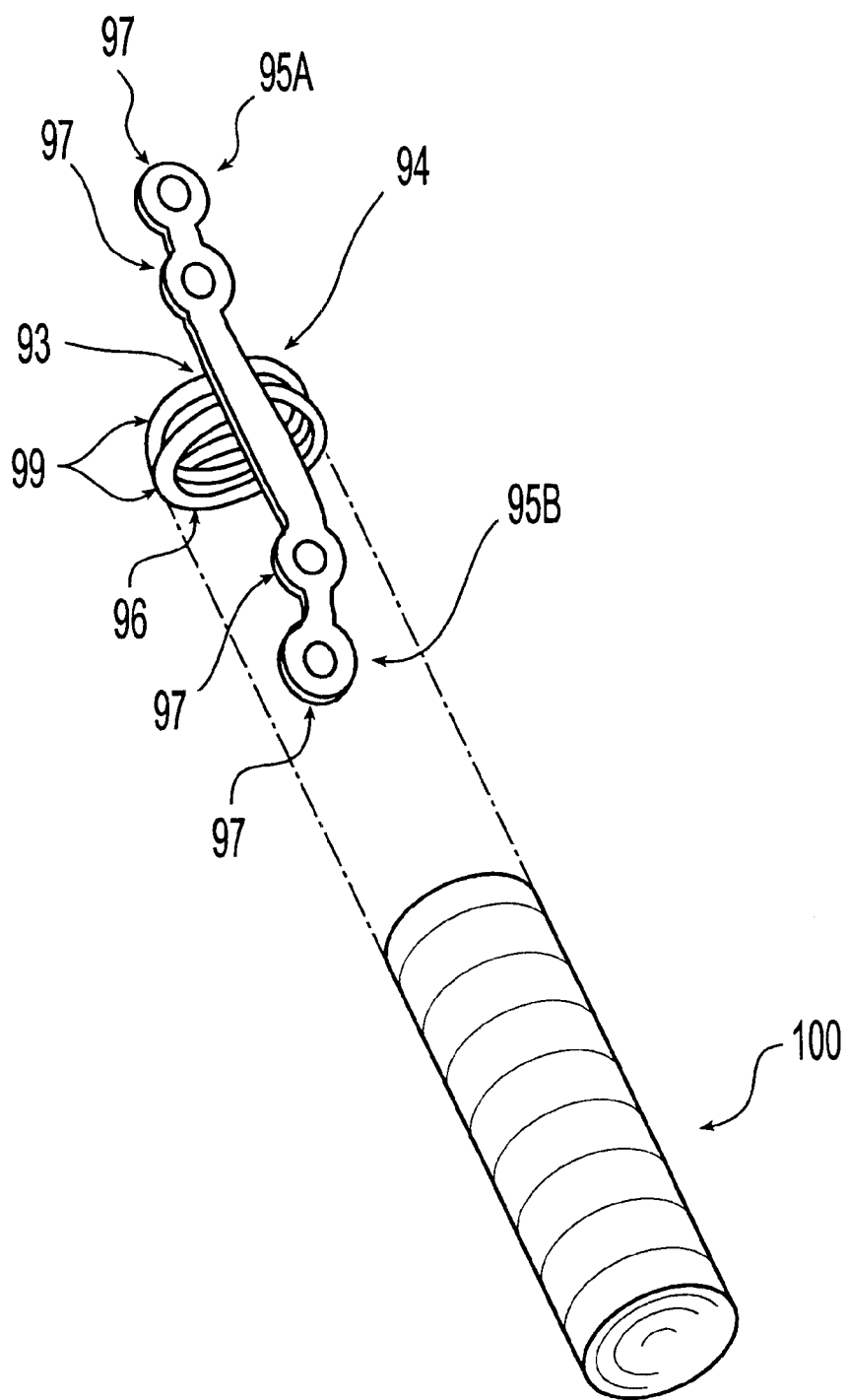
FIGS. 12A and 12B are perspective views of seventh and eighth embodiments of the implant, for use in unilateral laminoplasty procedures.
Figure 12B:
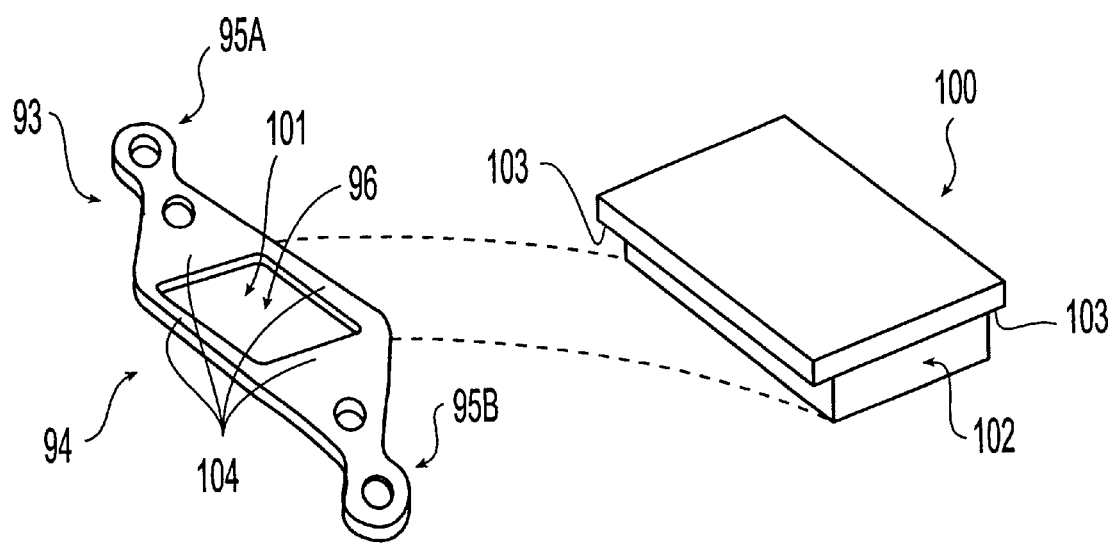

FIGS. 12A and 12B show implant embodiments comprising plates configured to attach directly to the opposing cut segments of lamina produced during a unilateral laminoplasty. These plates are further configured to capture segments of allograft and to engage these segments with the opposing cut segments of lamina to facilitate fusion between the implant and the patient's bone. Plate 93 comprises a body portion 94 having a longitudinal axis and first and second ends 95A, 95B, and a graft retaining portion 96, midway between the ends 95A, 95B, preferably approximately midway between ends 95A, 95B. First and second ends 95A, 95B each comprise a bone engaging portion 97. In a preferred embodiment the bone engaging portion at each first and second end comprises at least one hole suitable for receiving a bone screw 98 (not shown). The bone screws are then used to secure the plate 93 to each opposing segment of lamina. In a further embodiment the bone engaging portions may be hooks capable of grasping bone screws that are installed in the lamina segments.

In the embodiment shown in FIG. 12A, the graft retaining portion 96 comprises a plurality of deformable fingers 99 which are initially arrayed flat along an axis perpendicular to the longitudinal axis of the plate 93. These fingers 99 are capable of being deformed to cradle an allograft 100, preferably cylindrical in shape. Allograft 100 preferably has a length sufficient to engage the cut ends of lamina upon installation, and a diameter of size sufficient to be captured by the deformed fingers 99 of the plate 93.

In the embodiment of FIG. 12B, plate 93 has a graft retaining portion 96 which comprises a hollow region 101, preferably rectangular in shape. A correspondingly configured allograft of cancellous bone is provided having a body 102 capable of being received within the hollow region 101, and further having shoulders 103 which extends beyond the hollow region to contact seating surface 104. In a preferred embodiment, shoulders 103 of allograft 100 are secured to plate 93 using a bone screw 98 placed through bone engaging portion 97.

In a preferred embodiment the plate 93 may be flexible to allow the surgeon to form the body 94 to the individual contour of the patient's spine, thereby achieving a tight fit between components. The plate 93 may be fabricated from a biocompatible metal or other material known in the art that would be suitable for long term retention of an implant and graft.

The current invention also provides a method of using an allograft implant according to any of the embodiments shown in FIGS. 1A, 5A, 8A, 10A or 11A which further has partially, substantially, or fully demineralized end segments to promote fusion between opposing segments of lamina or spinous process produced during a unilateral or bilateral laminoplasty procedure. This method comprises the steps of cutting a targeted lamina or spinous process as required for either a unilateral or bilateral laminoplasty procedure, separating the resulting segments of bone a sufficient distance to allow for insertion of an appropriately sized allograft implant, providing an allograft implant having bone engaging surfaces which comprise partially, substantially, or fully demineralized cortical bone to a depth of up to about 2 mm, and contacting the allograft implant bone engaging surfaces with respective cut segments of lamina or spinous process. This method may be augmented, in the case of a unilateral laminoplasty, to include the additional step of installing a plate over the allograft implant to further assist retention of the implant between the bone segments. Where such a plate is provided, the additional steps of providing bone screws or other fasteners to attach the plate to the opposing segments of bone and/or to attach the plate to the implant, may further be included.

A further embodiment of the above method comprises providing an allograft implant according to the above method, which implant further has partially, substantially, or fully demineralized bone flaps capable of receiving bone screws. Providing such an implant allows the surgeon to affirmatively secure the implant to the cut lamina segments, preferably without the need for a separate plate.

A method of installing a tri-cortical allograft implant as part of a bilateral laminoplasty procedure is also provided. This method comprises the steps of bisecting a targeted spinous process, providing hinge cuts on both adjacent lamina sufficient to allow the spinous process segments to be spread apart, separating the spinous process segments to allow for insertion of an appropriately sized allograft implant, providing an allograft implant having first and second angled bone engaging surfaces which approximate the angle between the bisected and spread spinous process segment cut surfaces, the allograft implant comprising cancellous bone material having a thin outer layer of cortical bone surrounding the cancellous bone, and which cortical bone layer is in communication with the first and second engaging surfaces so as to support the compressive stresses imparted by the cut spinous process segments.

A method of using only a screwed plate to maintain the distance between bone ends produced during a unilateral or bilateral laminoplasty procedure is also provided and described. This method comprises the steps of cutting a targeted lamina or spinous process as required for the respective laminoplasty procedure, separating the cut bone segments to increase the space available for the spinal canal and associated nerves, providing an appropriately sized plate having first and second ends, wherein each end is configured to allow engagement with the surface of the lamina opposite the surface of the spinal canal and adjacent the cut bone end, and securing first and second ends of the plate to the adjacent bone segments.

In a preferred embodiment of the method, each first and second end of the plate will have at least one recess suitable for receiving a bone screw, wherein the plate is secured to the adjacent cut bone ends using bone screws. In a further embodiment, two plates may be provided to attach to the adjacent cut bone ends.

Accordingly, it should be understood that the embodiments disclosed herein are merely illustrative of the principles of the invention. Various other modifications may be made by those skilled in the art which will embody the principles of the invention and fall within the spirit and the scope thereof.

What is claimed is:

1. An implant for use in the spinal column, the implant comprising:
   (a) an allograft fabricated from cancellous bone material and having a length,
   (b) a structual member formed of non-allograft material having first and second bone engaging portions, and an allograft engaging portion, wherein said allograft engaging portion is configured to retain the allograft when the allograft contacts the graft engaging portion, and wherein the member contacts the allograft along a substantial portion of the length of the allograft.

2. The implant of claim 1 wherein the graft engaging portion comprises at least one raised tab.

3. The implant of claim 2 wherein the member has a central region between the first and second bone engaging portions, the at least one raised tab angel inward toward the central region of the member.

4. The implant of claim 1 wherein the allograft comprises first and second ends, the first and second ends comprising bone engaging portions, wherein at least one of the bone engaging portions comprises demineralized bone.

5. The implant of claim 1 wherein at least one of the bone engaging portions comprises a suture attachment portion configured to allow a surgeon to secure the bone connecting portions to the first and second bone segment.

6. An implant for use in maintaining a desired distance between a first spinal bone having a first outer surface and a first cut bone end, and a second spinal bone having a second outer surface and a second cut bone end, said implant comprising:
   (a) an allograft having a body, the body having first and second ends,
   (b) a plate formed of non-allograft material having an intermediate portion and first and second ends, said intermediate portion having an allograft engaging portion configured to retain the allograft, said first and second plate ends comprising bone engaging portions, having fastener receiving portions,
wherein the allograft engaging portion is configured and adapted to engage the allograft body and the bone engaging portions are adapted and configured to engage the first and second bone outer surfaces and the allograft first and second ends are adapted and configured to contact the first and second cut bone ends, and wherein at least a portion of at least one of the bone engaging portions is deformable to allow shaping to the surface of the respective bone.

7. The implant of claim 6 wherein said allograft engaging portion comprises deformable fingers which are configured and adapted to engage the graft.

8. The implant of claim 6 wherein said allograft engaging portion comprises a hollow portion, and said allograft comprises a shape complementary to said hollow portion, the hollow portion adapted and configured to at least partially receive said allograft.

9. The implant of claim 6 wherein said allograft engaging portion comprises at least one screw hole capable of receiving a bone screw for securing said allograft to said graft engaging portion.

10. The implant of claim 6 wherein the allograft first and second ends comprise bone engaging portions, and wherein at least one of the bone engaging portions comprises demineralized bone.

11. A method of providing a desired distance between first and second cut bone ends of the spine, comprising the steps of:
   (a) cutting at least one segment of a vertebra to produce first and second cut bone ends;
   (b) separating the first and second cut bone ends to define a space therebetween;
   (c) providing an allograft having a body, the body having first and second ends;
   (d) providing a plate formed of a non-allograft material having an intermediate portion and first and second ends, said intermediate portion having an allograft engaging portion configured to retain the allograft, said first and second plate ends comprising bone engaging portions, having fastener receiving portions,
wherein the allograft engaging portion is configured and adapted to engage the allograft body and the bone engaging portions are adapted and configured to engage the first and second outer surfaces and the allograft first and second ends are adapted and configured to contact the first and second cut bone ends;
   (e) engaging the allograft engaging portions with the allograft;
   (f) engaging said bone engaging portions with said first and second cut bone ends;
   (g) deforming at least one bone engaging portion to conform to the outer surface of its respective cut bone segment;
   (h) providing at least two bone fasteners;
   (i) inserting at least one said bone fastener into the fastener receiving portion of each bone engaging portion; and
   (j) engaging the at least one bone fasteners with said cut bone ends.

12. The method of claim 11 wherein the step of providing a plate comprises providing a plate having a body comprising a plurality of holes suitable for receiving bone screws.

13. The method of claim 11 wherein the step of cutting comprises cutting all the way through one lamina of the vertebra.

14. The method of claim 13 wherein the step of cutting further comprises cutting half way through the adjacent lamina of the vertebra.

15. An implant for use in a laminoplasty procedure, the implant comprising:
   (a) an allograft fabricated from cancellous bone material,
   (b) a member formed of non-allograft material having first and second bone engaging portions and an allograft engaging portion, wherein said allograft engaging portion is configured to retain the allograft when the allograft contacts the allograft engaging portion, and wherein said bone engaging portions are configured to engage first and second bone ends produced during a laminoplasty procedure.

16. The implant of claim 15, wherein at least one of said first and second bone ends comprises a vertebral lamina.

17. The implant of claim 15, wherein the first and second bone engaging portions each further comprises at least one fastener receiving portion.

18. The implant of claim 15, wherein the non-allograft member comprises at least one suture receiving portion configured to receive a suture for securing the bone engaging portions to respective bone ends.

19. The implant of claim 15, wherein the first and second bone ends each has an outer surface, and at least one of the first and second bone engaging portions is deformable to allow shaping to its respective bone outer surface.

20. The implant of claim 15, wherein the allograft comprises first and second ends, the first and second ends comprising bone engaging portions, and wherein at least one of the bone engaging portions of the allograft comprises demineralized bone.

21. The implant of claim 15, wherein the allograft has a perimeter, and the allograft engaging portion contacts the allograft along a substantial portion of the perimeter.

22. An implant for use in the spinal column, the implant comprising:

(a) an allograft fabricated from cancellous bone material, (b) a member formed of non-allograft material having first and second bone engaging portions and an allograft engaging portion, wherein said allograft engaging portion is configured to retain the allograft when the allograft contacts the allograft engaging portion, and wherein at least a portion of said allograft engaging portion is deformable to allow shaping the allograft engaging portion to at least partly conform to the surface of the allograft.

23. The implant of claim 22, wherein the allograft engaging portion comprises deformable fingers configured to grip the allograft.

24. The implant of claim 22, wherein at least one of the first and second bone engaging portions is configured to engage a vertebral lamina.

25. The implant of claim 22, wherein the bone engaging portions further comprise fastener receiving portions.

26. The implant of claim 22, wherein the bone engaging portions comprise suture receiving portions configured to receive a suture for tying the bone engaging portion to a respective cut bone end.

27. The implant of claim 22, wherein the allograft comprises first and second ends, the first and second ends comprising bone engaging portions, and wherein at least one of the bone engaging portions of the allograft comprises demineralized bone.

28. The implant of claim 22, wherein the first and second cut bone segments each has an outer surface, and at least one of the first and second bone engaging portions is deformable to allow shaping to the respective outer surface.

29. A method of providing a desired distance between first and second cut bone ends produced during a laminoplasty procedure, comprising the steps of:

(a) performing a laminoplasty procedure to produce first and second cut bone ends of a single vertebra, each bone end having an outer bone surface;

(b) separating the first and second cut bone ends to define a space therebetween;

(c) providing an allograft having a body, the body having first and second ends;

(d) providing a plate formed of a non-allograft material having an intermediate portion and first and second ends, said intermediate portion having an allograft engaging portion configured to retain the allograft, said first and second plate ends comprising bone engaging portions, wherein the allograft engaging portion is configured and adapted to engage the allograft body and the bone engaging portions are adapted and configured to engage respective outer bone surfaces of the cut bone ends and the allograft first and second ends are adapted and configured to contact the first and second cut bone ends;

(e) engaging the allograft engaging portion with the allograft; and (f) engaging said bone engaging portions with said first and second cut bone ends.

30. The method of claim 29, wherein the step of performing a laminoplasty procedure comprises cutting at least one vertebral lamina.

31. The method of claim 29, wherein the bone engaging portions of the plate further comprise fastener receiving portions, the method further comprising, after step (f), the steps of:

(g) providing at least two bone fasteners;

(h) inserting at least one said bone fastener into the fastener receiving portion of each bone engaging portion; and (i) engaging the at least one bone fasteners with said cut bone ends.

32. The method of claim 29, wherein the step of providing a plate comprises providing a plate having an allograft engaging portion comprising deformable fingers to grip the allograft, and step (g) further comprises shaping the deformable fingers to grip the allograft.

* * * * *

UNITED STATES PATENT AND TRADEMARK OFFICE
CERTIFICATE OF CORRECTION

PATENT NO. : 6,635,087 B2
DATED : October 21, 2003
INVENTOR(S) : Angelucci et al.

It is certified that error appears in the above-identified patent and that said Letters Patent is hereby corrected as shown below:

<u>Title page,</u>
Item [75], Inventor, "Martin Walter" should read -- Martin Walther. --.

Signed and Sealed this

Twenty-seventh Day of April, 2004

JON W. DUDAS
*Acting Director of the United States Patent and Trademark Office*